United States Patent [19]

Baumann et al.

[11] 4,088,681

[45] May 9, 1978

[54] SUBSTITUTED 1-ALKENYNYL-CYCLOHEXANOLS AND -CYCLOHEXENES AND PROCESSES FOR THEIR PREPARATION

[75] Inventors: Manfred Baumann, Mannheim; Werner Hoffmann, Neuhofen, both of Germany

[73] Assignee: BASF Aktiengesellschaft, Ludwigshafen, Germany

[21] Appl. No.: 749,006

[22] Filed: Dec. 9, 1976

[30] Foreign Application Priority Data

Dec. 27, 1975 Germany .............................. 2558807
Dec. 27, 1975 Germany .............................. 2558806

[51] Int. Cl.² ...................... C07C 35/08; A61K 7/46; A61K 7/06
[52] U.S. Cl. ................................ 568/828; 260/666 R; 252/522; 424/69; 424/59; 424/70; 260/586 R; 260/666 P; 568/816
[58] Field of Search ............ 260/617 E, 631 R, 631.5, 260/666 AR, 575.5

[56] References Cited

U.S. PATENT DOCUMENTS

| | | | |
|---|---|---|---|
| 2,579,658 | 12/1951 | Evans .............................. | 260/631 R |
| 2,655,548 | 10/1953 | Evans et al. ..................... | 260/631 R |
| 2,775,626 | 12/1956 | Schaaf et al. .................... | 260/631 R |
| 3,236,869 | 2/1966 | Thompson ....................... | 260/631 R |
| 3,527,815 | 9/1970 | Holty .............................. | 260/631 R |
| 3,769,330 | 10/1973 | Nikawitz et al. ................ | 260/631 R |
| 3,801,653 | 4/1974 | Pasedoch et al. ................ | 260/631 R |
| 3,946,078 | 3/1976 | Routenstrauch et al. ....... | 260/631 R |

*Primary Examiner*—James O. Thomas, Jr.
*Assistant Examiner*—James H. Reamer
*Attorney, Agent, or Firm*—Keil, Thompson & Shurtleff

[57] ABSTRACT

New substituted 1-alkenynyl-cyclohexanols and 1-alkenynyl-cyclohexenes. The 1-alkenynyl-cyclohexanols are obtained by reacting the corresponding cyclohexanone witn an enyne in the presence of a strongly basic condensing agent in an inert solvent, or with an alkali metal salt of an enyne in an inert solvent. The 1-alkenynyl-cyclohexenes are obtained by dehydrating the 1-alkenynyl-cyclohexanols or 1-cycloalkanolyl-alkynols. The new compounds are themselves interesting scents, but can also be used as starting materials for further interesting scents.

5 Claims, No Drawings

SUBSTITUTED 1-ALKENYNYL-CYCLOHEXANOLS AND -CYCLOHEXENES AND PROCESSES FOR THEIR PREPARATION

The present invention relates to substituted 1-alkenynyl-cyclohexanols and -cyclohexenes of the general formula I

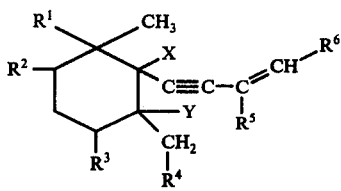

where $R^1$ to $R^4$ are H or $-CH_3$ and $R^5$ and $R^6$ are H or a saturated or olefinically unsaturated aliphatic hydrocarbon radical of 1 to 6 carbon atoms, which is not substituted by hetero-atoms, and are preferably H, $CH_3$ or $C_2H_5$, or alternatively $R^5$ and $R^6$ together are optionally alkyl-substituted alkylene of 3 to 7 carbon atoms and X is OH if Y is H (Ia), or X and Y together are an additional bond between the carbon atoms on which they are present (Ib). More especially, the invention relates to those 1-alkenynyl-cyclohexanols of the formula I, where $R^5$ and $R^6$ together contain at most 6 carbon atoms.

The new 1-alkenynyl-cyclohexanols of the formula I have a fresh, woody and tart coniferous odor and can therefore be used as constituents of scent compositions, or to improve the odor of industrial products. Furthermore, they offer a new and economical method of obtaining the β-damascones, which are popular scents, since the former compounds are themselves relatively easily accessible and can be converted simply, by heating in the presence of acids, to the corresponding β-damascones. This method has a great advantage over the method of manufacture of β-damascones by acid-catalyzed reaction of 2,2,6-trimethyl-1-(3'-hydroxybut-1'-yn-1'-yl)-cyclohexanol, as disclosed in the literature, in that the conventional method results in a mixture of the β-damascones with spiro compounds, which are very difficult to separate off.

The new substituted 1-alkenynyl-cyclohexenes in most instances have an intense spicy, woody-tart and sometimes floral odor and are therefore outstandingly suitable for use as scents with a tart note. They accordingly provide the perfumer with further scope for compounding valuable scent compositions. Synthetic scent compositions are of particular importance in the cosmetics industry, for the production of lotions, hair lotions, creams, powders, aerosols and the like, and also of particular importance for use as industrial perfumes for masking the unpleasant intrinsic odor of a plurality of raw materials.

The present invention further relates to a process for the manufacture of the substituted 1-alkenynyl-cyclohexanols of the formula I, wherein cyclohexanones of the general formula II

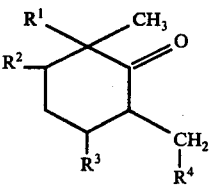

where $R^1$ to $R^4$ have the above meanings, are reacted with an enyne of the general formula III

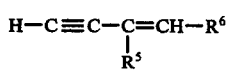

where $R^5$ and $R^6$ have the above meanings, in the presence of a strongly basic condensing agent, in an inert solvent, or are reacted with an alkali metal salt of an enyne of the formula III in an inert solvent.

The cyclohexanones of the formula II required as starting materials for the process of the invention are conventional compounds which may be manufactured by alkylating cyclohexanones, or hydrogenating cyclohexenones which in turn may be manufactured from aliphatic ketones and α,β-unsaturated carbonyl compounds. Examples of useful cyclohexanones of the formula III are 2,3,6-trimethyl-cyclohexanone, 2,6-dimethyl-cyclohexanone, 2,2,6-trimethyl-cyclohexanone, 2,2,3,6-tetramethyl-cyclohexanone, 2,2,5-trimethyl-6-ethyl-cyclohexanone and 2,2-dimethyl-6-ethyl-cyclohexanone.

The enynes of the formula III may be manufactured simply, by dehydrating ethynyl-alcohols, which in turn are readily accessible by ethynylating carbonyl compounds.

Examples of useful enynes of the formula III are methylbutenyne, 3-methyl-pent-1-yn-4-ene, ethylbutenyne, ethynylcyclohexene, 2,6-dimethyl-oct-2,5-dien-7-yne, 2-methyl-6-methylene-oct-2-en-7-yne, vinylacetylene, 2,6-dimethyl-oct-1,5-dien-7-yne and 2,6-dimethyl-oct-1,3,5-trien-7-yne, preferably methylbutenyne and vinylacetylene. The enynes of the formula III need not be employed as such. Instead of using the enynes in the presence of a strongly basic condensing agent, the active salts of the enyne may be used directly. This is very advisable, for example, when using the unsubstituted enyne of the formula III, since vinylacetylene itself is difficult to handle. In that case Na-vinylacetylide, for example, is used; it can be obtained simply, by the action of Na on 1,4-dichloro-2-butene in liquid $NH_3$.

Strongly basic condensing agents suitable for the reaction of the invention are alkali metal hydroxides, e.g. NaOH and KOH, alkali metal alcoholates, e.g. $NaOCH_3$, $KOC_2H_5$ and K tert.-butylate, alkali metal-organyl compounds, e.g. n-butyl lithium, alkaline earth metal-organyl compounds, e.g. $CH_3MgCl$, alkali metal hydrides, e.g. KH and NaH, and alkali metal amides, e.g. $NaNH_2$ and $KNH_2$.

Preferred basic condensing agents are $CH_3MgCl$, NaOH, potassium isobutylate and KOH.

The more weakly basic is the condensing agent employed, the more adverse is the reaction equilibrium, from the point of view of the desired reaction. It is particularly advantageous to use $CH_3MgCl$, since in that case the evolution of CH₄ shifts the equilibrium greatly in favor of the desired reaction.

The basic condensing agents are in general employed in molar to 5-molar amounts.

Examples of inert solvents suitable for use in the process of the invention are ethers, e.g. diethyl ether, diisopropyl ether, diethylene glycol dimethyl ether and tetrahydrofuran (THF), aliphatic hydrocarbons, e.g. n-hexane, n-heptene and cyclohexane; aromatic hydrocarbons, e.g. benzene, xylene and toluene, amides, e.g. dimethylformamide, N-methylpyrrolidone and hexamethylphosphotriamide and amines, e.g. NH₃.

The use of NH₃, THF and toluene is preferred.

The procedure followed for carrying out the process of the invention is in general either first to add the enyne of the formula III to the suspension of the strongly basic condensing agent in the solvent which is inert under the reaction conditions, then to add the cyclohexanone of the formula II and allow the reaction mixture to finish reacting at the reaction temperature, or to introduce a mixture of the cyclohexanone of the formula II and the enyne of the formula III very slowly into the suspension of the basic condensing agent and allow the reaction mixture to finish reacting at the reaction temperture.

The reaction temperature may be from $-50°$ to $+100°$ C, preferably from $-20°$ to $+50°$ C.

Reaction time is from a few hours to several days, depending on the reactant, condensing agent and temperature.

The reaction mixture is worked up by conventional methods, e.g. by washing out the inorganic constituents (if necessary after neutralizing the reaction batch with acids, e.g. HCOOH, CH₃COOH, HCl, H₂SO₄ or CO₂), removing the solvent and fractionally distilling the material.

2,2,6-Trimethyl-1-(3'-methyl-but-1'-yn-3'-en-1'-yl)-cyclohexanol should be mentioned particularly as compounds which can be manufactured by the process of the present invention. They have a fresh, woody-tart coniferous odor and can therefore be used as scents. They are furthermore important because they can be used to manufacture β-damascones of the general formula IV

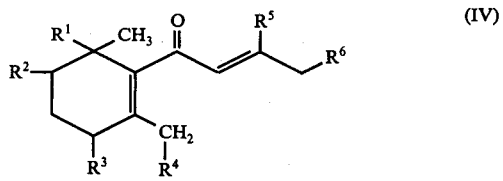

where R¹ to R⁶ have the above meanings, by acid-catalyzed rearrangement, resembling the Rupe rearrangement. Acid catalysts which may be used are, in principle, all acids which are as strongly acid as HCOOH or more strongly acid than HCOOH and which do not attack the reactants in other ways under the reaction conditions. Examples of acid catalysts or reaction systems for this rearrangement are HCOOH in concentrations of from 70 to 97%, HCOOH in CH₃OH, mixtures of H₂SO₄ and CH₃COOH, ion exchangers, e.g. Dowex 50 in CH₃COOH, aqueous H₂SO₄ of various concentrations, H₂SO₄ in ethanol, 2-propanol or n-butyl ether, a mixture of phosphoric acid and acetic acid, phenol, malic acid, maleic acid, malonic acid, chloroacetic acid, trichloroacetic acid, benzenesulfonic acid and ZnCl₂.

Examples 12 and 13 describe the experimental details of carrying out this rearrangement.

Regarding further details of this conventional rearrangement of tertiary acetylene-alcohols to give α,β-unsaturated carbonyl compounds, reference may be made to Chem.Reviews 71 (1971) No. 5., pages 429 et seq.

The invention further relates to a process for the manufacture of the new substituted 1-alkenynyl-cyclohexenes of the formula I, wherein the 1-alkenynyl-cyclohexanols of the invention, of the general formula Ia

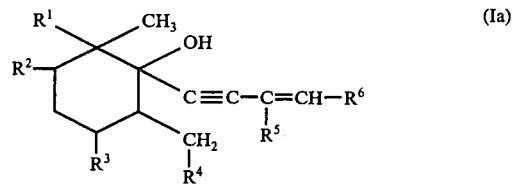

where R¹ to R⁶ have the above meanings, or substituted 1-cycloalkanolyl-alkynols of the general formula V

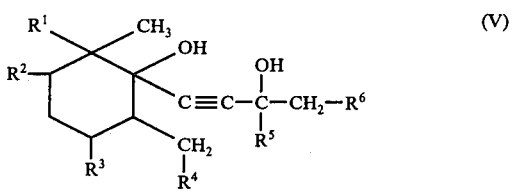

where R¹ to R⁶ have the above meanings, are exposed to the conventional conditions for dehydration of alcohols.

The 1-cycloalkanolyl-alkynols of the formula II required as starting materials, in addition to the 1-alkenynyl-cyclohexanols of the formula Ia, can be manufactured simply, from the corresponding cyclohexanones, by basic condensation with the corresponding alkynols.

In general, 3 variants of the process for dehydrating alcohols are employed:

a. the dehydration of alcohols with acid dehydrating agents in the liquid phase, b. catalytic dehydration in the gas phase and c. dehydration over acid ion exchangers in suspension.

The first variant is particularly recommended for fairly small reaction batches, whilst the second variant has above all proved of value on an industrial scale.

Acid dehydrating agents used for dehydrating alcohols in the liquid phase are, in the main, proton acids, e.g. H₂SO₄, H₃PO₄, H₃BO₃, oxalic acid, formic acid, p-toluenesulfonic acid and naphthalene-2-sulfonic acid, Lewis acids, e.g. BF₃, anhydrous ZnCl₂ or CuSO₄, strongly acid ion exchangers, e.g. all ion exchangers containing —SO₃H groups, and dehydrating agents, e.g. acetic anhydride, POCl₃ in pyridine or acid aluminum oxide. Since the starting compounds are tertiary alcohols, which, furthermore, are activated by the presence of multiple bonds, relatively mild dehydration conditions suffice for the reaction according to the invention. The use of mild reaction conditions is furthermore advisable because the products, especially the compounds containing hydroxyl groups, can, under more severe conditions, undergo rearrangement — at least partially — to the corresponding β-damascones. Thus, the water-soluble acids are in general used in a dilute aqueous form, e.g. as H₂SO₄ of from about 15 to 50% strength, aqueous HCl of from about 10 to 18% strength of HCOOH of from 40 to 80% strength. If, for example, aqueous sulfuric acid is used, virtually no β-damascones are formed at acid concentrations of less than 60% by weight and temperatures below 100° C. Similar remarks apply to the use of 80% strength by weight HCOOH and temperatures of below 90° C, whilst at temperatures above 90° C, and when using 80% strength HCOOH, up to 40% of β-damascones can be obtained. On the other hand, the reaction is not as temperature-dependent if dilute HCOOH is used. If water-insoluble acid dehydrating agents are used, the dehydration is advantageously carried out in an inert organic solvent. Examples of inert solvents which may be used are aliphatic hydrocarbons, e.g. hexane, heptane, cyclohexane and decalin, aromatic hydrocarbons, e.g. benzene, toluene, xylene and tetralin, and halohydrocarbons, e.g. chlorobenzene, CHCl₃, CH₂Cl₂ and CCl₄.

The reaction temperature is from 20 to about 150° C, preferably from 50° to 100° C, depending on the starting compound and on the dehydrating agent. The reaction time can be from a few minutes to several hours.

Catalysts used for the dehydration of alcohols in the vapor phase are above all the oxides of Al, Th, Ti and W, as well as silica, boric acid and certain acid phosphates. The reaction temperature in the gas phase is from about 250° to 350° C and the reaction times are substantially shorter than in the case of the liquid process and are from about 0.01 second to 1 minute, preferably from 0.1 second to 30 seconds.

Regarding further details of the dehydration of alcohols, reference may be made to Houben-Weyl "Methoden der Organischen Chemie" 4th edition, volume 5/1 b, pages 45 et seq. and 70 et seq.

The new substituted 1-alkenynyl-cyclohexenes are distinguished by intense spicy, woody-tart notes and can therefore be used in the scent industry. Using the process of the invention, new interesting scents are obtained simply and from new starting materials.

The following compounds are of particular importance:

2,6,6-trimethyl-1-(3'-methyl-but-1'-yn-3'-en-1'-yl)-cyclohex-1-ene,
2,6,6-trimethyl-1-(but-1'-yn-3'-en-1'-yl)-cyclohex-1-ene,
2,3,6-trimethyl-1-(3',6'-dimethyl-oct-1'-yn-3',6'-dien-1'-yl)-cyclohex-1(6)-ene,
2,2,6-trimethyl-1-(3',7'-dimethyl-oct-1'-yn-3',5',7'-trien-1'-yl)-cyclohex-5-ene and
1-(2',2',6'-trimethyl-cyclohex-5'-en-1'-yl)-2-(cyclohex-1-en-1'-yl)-acetylene.

EXAMPLE 1

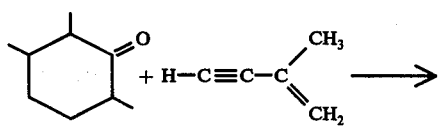

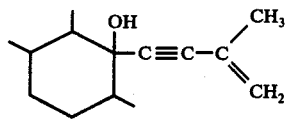

A solution of CH₃MgCl in THF is prepared by passing methyl chloride into a suspension of 19 g of Mg filings in 500 ml of tetrahydrofuran (THF). 50 g of methylbutenyne are added dropwise thereto in the course of 50 minutes at 0° C. The reaction mixture is then stirred until the evolution of gas has ceased. 105 g of 2,3,6-trimethylcyclohexanone are then added dropwise at room temperature and whilst cooling, and the reaction mixture is left overnight, whilst being stirred, in order to complete the reaction.

120 ml of water are then added dropwise and the organic phase is decanted, concentrated and subjected to fractional distillation.

93.5 g (corresponding to 61% of theory, based on trimethyl-cyclohexanone employed) of 2,3,6-trimethyl-1-(3'-methyl-but-1'-yn-3'-en-1'-yl)-cyclohexanol of boiling point 72° C/0.1 mm Hg are obtained. The spectroscopic data confirm the structure.

Fragrance note: fresh, herbaceous.

EXAMPLE 2

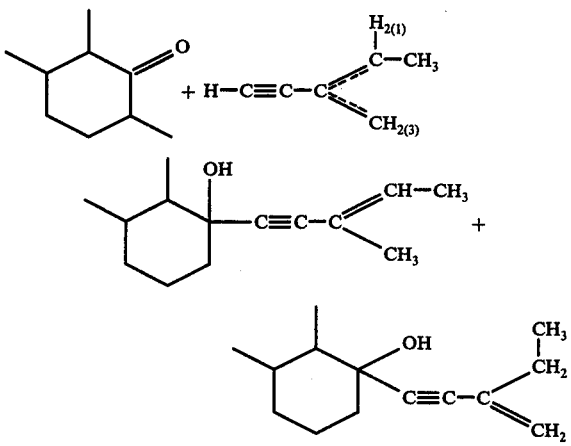

A mixture of 56 g of 2,3,6-trimethyl-cyclohexanone and 32 g of the isomer mixture (consisting of 3-methyl-pent-1-yn-3-ene and 3-methylene-1-pentyne in the molar ratio of about (1:1) obtained by eliminating water from 3-methyl-pent-1-yn-3-ol are added dropwise to 70 g of KOH powder, suspended in 200 ml of toluene, at 0° C, and the reaction mixture is stirred for 6 hours at 0° C. It is then neutralized with glacial acetic acid, washed with water, dried and concentrated.

Fractional distillation gives 15.2 g of unconverted 2,3,6-trimethyl-cyclohexanone and 53.7 g of a mixture of 2,3,6-trimethyl-1-(3'-methyl-pent-1'-yn-3'-en-1'-yl)-cyclohexanol and 2,3,6-trimethyl-1-(3'-methylene-pent-1'-yn-1'-yl)-cyclohexanol of boiling point 127°–129° C/8 mm Hg and refractive index $n_D^{25} = 1.4923$. This corresponds to a yield of 82% of theory, based on trimethylcyclohexanone converted. The spectroscopic data confirm the structure. Fragrance note: fresh, herbaceous.

EXAMPLE 3

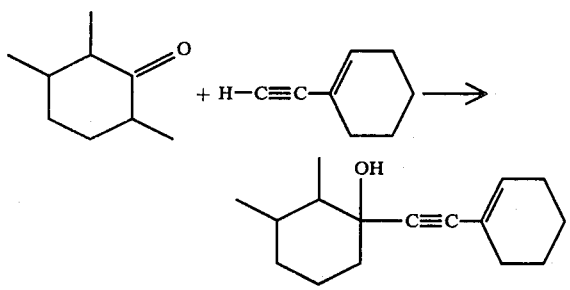

21.5 g of ethynylcyclohexene are added dropwise to a suspension of 6 g of 80% strength sodium hydride in 200 ml of tetrahydrofuran under reflux, and the reaction mixture is kept under reflux conditions until no further gas is evolved. 28 g of 2,3,6-trimethyl-cyclohexanone are then added dropwise at room temperature and the mixture is left overnight, whilst being stirred, in order to complete the reaction. Water is added to the reaction mixture, the reaction product is taken up in ether and the ether solution is washed with water, dried and concentrated. Fractional distillation gives 9 g of unconverted ethynylcyclohexene, 8 g of starting ketone, and 22 g of 1-(2,3,6-trimethyl-1-hydroxy-cyclohexyl)-2-(cyclohex-1-en-1-yl)-acetylene of boiling point 120° C/0.1 mm Hg and refractive index $n_D^{25} = 1.5143$. This corresponds to a yield of 68% of theory, based on trimethylcyclohexanone converted. Fragrance note: faint, tart, herbaceous.

EXAMPLE 4

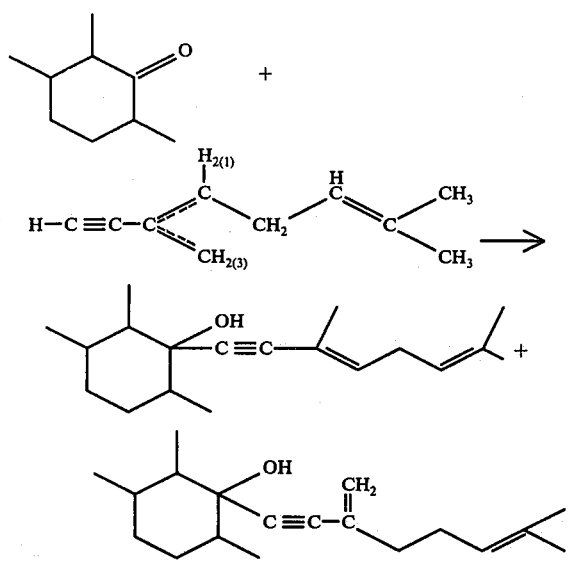

A mixture of 28 g of 2,3,6-trimethyl-cyclohexanone and 27 g of the isomer mixture consisting of 2,6-dimethyl-oct-2,5-dien-7-yne and 2-methyl-6-methylene-oct-2-en-7-yne, obtained by elimination of water from 2-dehydrolinalool, is added dropwise to a suspension of 35 g of KOH in 200 ml of toluene at 0° C. The reaction mixture is then kept for 6 hours at 0° C, whilst being stirred, after which water is added and the organic phase formed is dried and concentrated. Subsequent fractional distillation gives 12.3 g of unconverted trimethylcyclohexanone and 12 g of a mixture of 2,3,6-trimethyl-1-(3',7'-dimethyl-oct-1'-yn-3',6'-dien-1'-yl)-cyclohexanol and 2,3,6-trimethyl-1-(7'-methyl-3'-methylene-oct-1'-yn-6'-en-1'-yl)-cyclohexanol of boiling point 125°-127° C/0.4 mm Hg as a viscous oil. This corresponds to a yield of 39%, based on ketone converted. Fragrance note: faintly floral, spicy, minty.

EXAMPLE 5

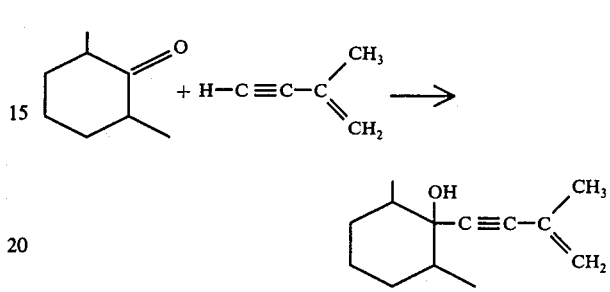

A solution of CH₃MgCl in THF is prepared by passing CH₃Cl into a suspension of 7.5 g of Mg filings in 150 ml of THF. 22 g of methylbutenyne are added dropwise at 0° C and the reaction mixture is stirred until the evolution of gas has ceased. 38 g of 2,6-dimethyl-cyclohexanone are then added dropwise, whilst cooling, and the mixture is stirred overnight at room temperature.

The mixture is worked up by the method described in Example 1. 43.5 g of 2,3,6-trimethyl-1-(3'-methyl-but-1'-yn-3'-en-1'-yl)-cyclohexanol of boiling point 63° C/0.2 mm Hg are obtained. The yield is 75% of theory, based on ketone employed.

Fragrance note: fresh, tart-woody.

EXAMPLE 6

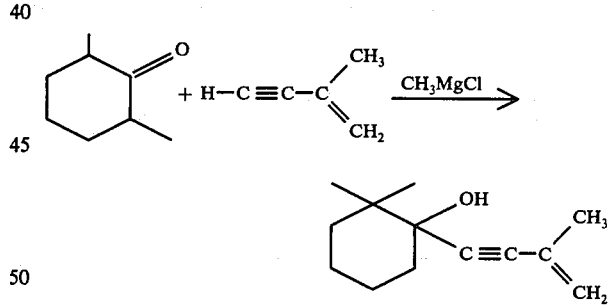

17 g of methylbutenyne are added dropwise at 0° C to a solution of CH₃MgCl prepared by introducing CH₃Cl into a suspension of 5 g of Mg filings in 100 ml of THF.

When the evolution of gas has ceased, 25 g of 2,2,6-trimethyl-cyclohexanone are added dropwise and the reaction mixture is stirred overnight. It is worked up by the method described in Example 1.

Fractional distillation gives 30.6 g (corresponding to 83% of theory, based on ketone employed) of 2,2,6-trimethyl-1-(3'-methyl-but-1'-yn-3'-en-1'-yl)-cyclohexanol of boiling point 65° C/0.1 mm Hg and refractive index $n_D^{25} = 1.4935$.

The spectroscopic data and the CH analysis confirm the structure. Fragrance note: fresh, tart-woody, coniferous.

EXAMPLE 7

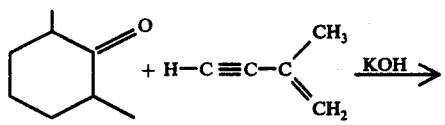

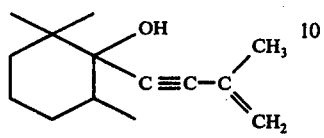

A mixture of 56 g of 2,2,6-trimethyl-cyclohexanone and 27 g of methylbutenyne is added dropwise to a suspension of 70 g of KOH powder in 200 ml of toluene at 0° C. The reaction mixture is stirred for 6 hours, 200 ml of water are added and the organic phase formed is neutralized, dried and concentrated.

Subsequent fractional distillation gives 12 g of unconverted trimethylcyclohexanone and 51.2 g of 2,2,6-trimethyl-1-(3'-methyl-but-1'-yn-3'-en-1'-yl)-cyclohexanol. This corresponds to a yield of 79% of theory, based on trimethyl-cyclohexanone converted.

EXAMPLE 8

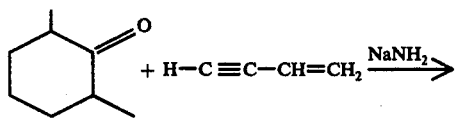

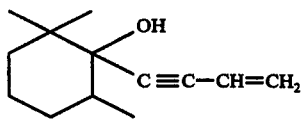

28 g of 2,2,6-trimethyl-cyclohexanone are added dropwise to a suspension of Na vinylacetylide (prepared from 25 g of 1,4-dichlorobut-2-ene and 15 g of Na in liquid ammonia) in 200 ml of THF, whilst cooling, and the reaction mixture is stirred overnight at room temperature. 50 ml of water are then added, the aqueous phase is extracted with ether and the resulting organic phase is dried and concentrated. Subsequent fractional distillation gives 5.5 g of unconverted trimethylcyclohexanone and 20.7 g (corresponding to 68% of theory, based on ketone converted) of 2,2,6-trimethyl-1-(but-1'-yn-3'-en-1'-yl)-cyclohexanol of boiling point 62°-63° C/0.3 mm Hg and refractive index $n_D^{25}$ = 1.4982. Fragrance note: fresh, tart-woody, coniferous.

EXAMPLE 9

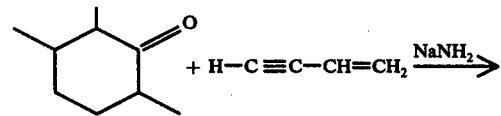

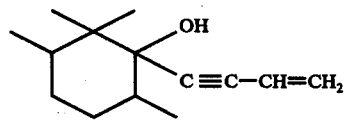

If the procedure of Example 8 is followed but instead of 28 g of 2,2,6-trimethyl-cyclohexanone 31 g of 2,2,3,6-tetramethyl-cyclohexanol are employed, fractional distillation gives 9.6 g of unconverted tetramethyl-cyclohexanone and 21 g (corresponding to 73% of theory, based on ketone converted) of 2,2,3,6-tetramethyl-1-(but-1'-yn-3'-en-1'-yl)-cyclohexanol of boiling point 66°-67° C/0.2 mm Hg and refractive index $n_D^{25}$ = 1.5018. Fragrance note: faintly floral, coniferous, fruity.

EXAMPLE 10

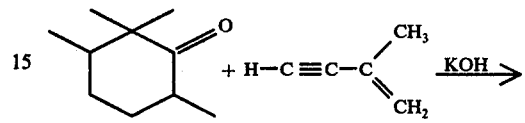

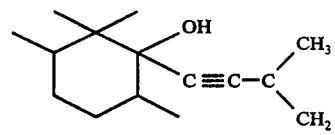

A mixture of 31 g of 2,2,3,6-tetramethyl-cyclohexanone and 15 g of methylbuteneyne is added dropwise in the course of 20 minutes to a suspension of 35 g KOH powder in 200 ml of ether at 0° C.

The reaction mixture is stirred for 6 hours at 0° C, 300 ml of water are then added and the aqueous phase is separated off. The organic phase is dried and concentrated.

Subsequent distillation gives 12 g of unconverted tetramethyl-cyclohexanone and 21 g (corresponding to 80% of theory, based on ketone converted) of 2,2,3,6-tetramethyl-1-(3'-methyl-but-1'-yn-3'-en-1'-yl)-cyclohexanol of boiling point 85°-86° C/0.4 mm Hg and refractive index $n_D^{25}$ = 1.4946. Fragrance note: spicy, tart-woody, coniferous.

EXAMPLE 11

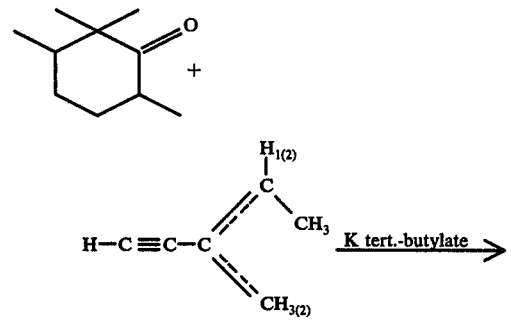

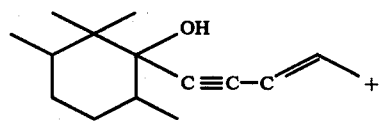

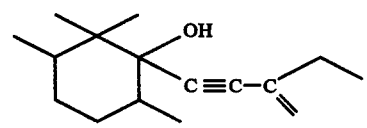

18 g of methylpentenyne are added dropwise to a suspension of 23 g of K tert.-butylate in 200 ml of THF at 0° C. 31 g of 2,2,3,6-tetramethylcyclohexanone are then added dropwise and the solution is stirred for 6 hours at 0° C. 50 ml of water are then added, the aqueous phase is extracted with ether and the combined organic phases are washed neutral, dried and concentrated. Subsequent fractional distillation gives 7.3 g of unconverted tetramethyl-cyclohexanone and 30.7 g (corresponding to 85% of theory, based on ketone converted) of a mixture of 2,2,3,6-tetramethyl-1-(3'-methyl-pent-1'-yn-3'-en-1'-yl)-cyclohexanol and 2,2,3,6-tetramethyl-1-(3'-methylene-pent-1'-yn-1'-yl)-cyclohexanol of boiling point 84°–85° C/0.3 mm Hg and refractive index $n_D^{25} = 1.4989$. Fragrance note: spicy, tart-woody, coniferous.

EXAMPLE 12

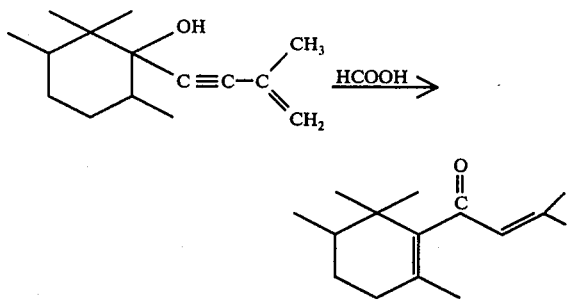

22 g of 2,2,3,6-tetramethyl-1-(3'-methyl-but-1'-yn-3'-en-1'-yl)-cyclohexanol, described in Example 10, and 100 ml of 60% strength formic acid are heated for 3 hours at 90° C. The mixture is then diluted to twice its volume with water and is extracted with hexane, and the extract is washed with water, dried and concentrated. Fractional distillation gives 9.5 g (corresponding to 42% theory) of the corresponding β-damascone (2,2,3,6-tetramethyl-1-(1'-oxo-3'-methyl-but-2'-en-1'-yl)-cyclohexene) of boiling point 82°–85° C/0.25 mm Hg, having the scent typical of such products.

EXAMPLE 13

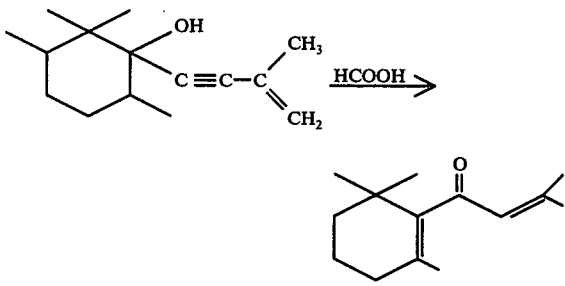

16 g of the acetylene-alcohol described in Example 6 are added dropwise, at 95° C, to 80 ml of 80% strength formic acid. The reaction mixture is kept for 1 hour at this temperature. The formic acid is then distilled off under reduced pressure, the residue is taken up in ether and the ether solution is washed, dried and distilled.

6.4 g (corresponding to 40% of theory) of the corresponding β-damascone (2,2,6-trimethyl-1-(1'-oxo-3'-methyl-but-2'-en-1'-yl)-cyclohexene) of boiling point 73°–76° C/0.3 mm Hg are obtained.

EXAMPLE 14

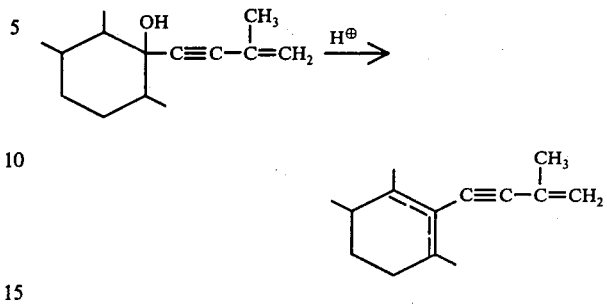

93 g of 2,3,6-trimethyl-1-(3'-methyl-but-1'-yn-3'-en-1'-yl)-cyclohexanol are added dropwise in the course of 15 minutes to 200 ml of a 60% strength aqueous HCl solution at 60° C and the resulting mixture is stirred for 2 hours at 60° C. It is then extracted with hexane and the hexane phase is washed neutral with sodium bicarbonate solution, dried and concentrated. Subsequent fractional distillation gives 63.3 g (corresponding to 74% of theory) of a mixture of 2,3,6-trimethyl-1-(3'-methyl-but-1'-yn-3'-en-1'-yl)-cyclohex-1-ene and 2,3,6-trimethyl-1-(3'-methyl-but-1'-yn-3'-en-1'-yl)-cyclohex-6-ene of boiling point 61°–64° C/0.2 mm Hg and refractive index $n_D^{25} = 1.5170$.

The spectroscopic data and CH analysis confirm the indicated structure.

EXAMPLE 15

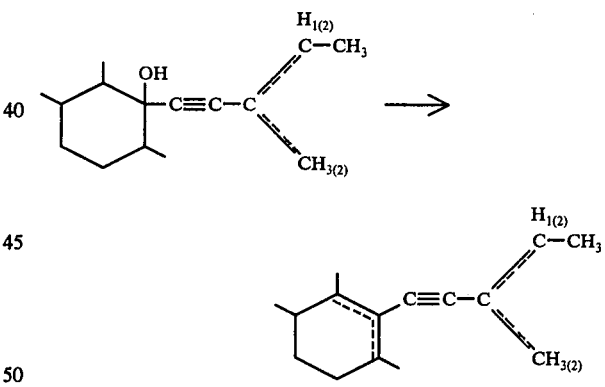

25 g of a mixture of 2,3,6-trimethyl-1-(3'-methyl-pent-1'-yn-3'-en-1'-yl)-cyclohexanol and 2,3,6-trimethyl-1-(3'-methylene-pent-1'-yn-1'-yl)-cyclohexanol are heated to the boil with 1 g of p-toluenesulfonic acid in 100 ml of chloroform, under a water separator. In the course of 60 minutes, 2 g of water are separated off. The solution is washed neutral with sodium bicarbonate, dried and concentated. Subsequent fractional distillation gives 11 g of the 1-alkenyl-cyclohexene shown above (corresponding to 48% of theory), of boiling point 75°–77° C/0.3 mm Hg. The IR-spectroscopic data and NMR-spectroscopic data, and the elementary analysis confirm the structure, and the gas chromatogram indicates an isomer pair. Fragrance note: woody, balsamic, slightly sweet.

EXAMPLE 16

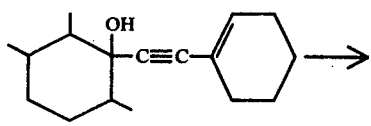

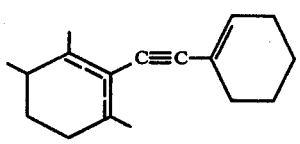

22 g of 1-(1'-hydroxy-2',3',6'-trimethyl-1-cyclohexyl)-2-(cyclohex-1en-1-yl)-acetylene are heated with 80 ml of 60% strength HCOOH for 30 minutes at 80° C. The mixture is then extracted with petroleum ether and the organic solution is neutralized with NaHCO$_3$ solution, dried and concentrated. Subsequent fractional distillation gives 15 g (corresponding to 74% of theory) of 1-(2',3',6'-trimethyl-cyclohex-1'(6')-en-1'-yl)-2-(cyclohex-1-en-1-yl)-acetylene of boiling point 115°–116° C/0.3 mm Hg and refractive index $n_D^{25} = 1.5348$. Fragrance note: balsamic, green, slightly leathery.

EXAMPLE 17

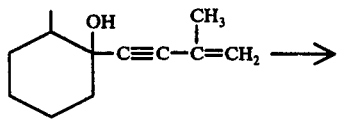

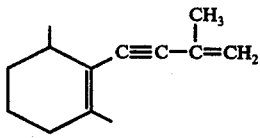

43 g of 2,6-dimethyl-1-(3'-methyl-but-1'-yn-3'-en-1'-yl)-cyclohexanol are added dropwise, at 80° C, to 200 ml of 50% strength H$_2$SO$_4$. The reaction mixture is then stirred for 1 hour at 80° C and extracted with petroleum ether and the petroleum ether extract is washed, dried and concentrated. Subsequent fractional distillation gives 19 g (corresponding to 49% of theory) of 2,6-dimethyl-1-(3'-methyl-but-1'-yn-3'-en-1'-yl)-cyclohex-1-ene of boiling point 58°–60° C/0.2 mm Hg. Scent: resembles turpentine oil.

EXAMPLE 18

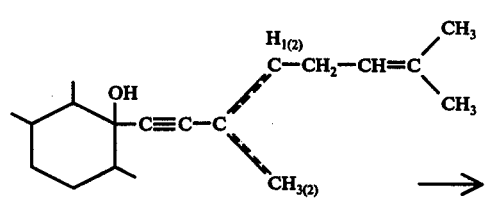

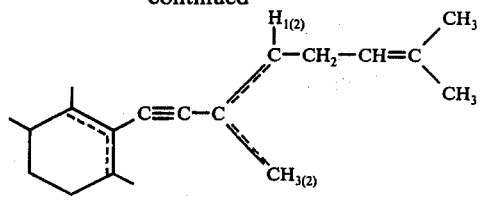

12 g of a mixture of 2,3,6-trimethyl-1-(3',7'-dimethyl-oct-1'-yn-3',6'-dien-1'-yl)-cyclohexanol and 2,3,6-trimethyl-1-(7'-methyl-3'-methylene-oct-1'-yn-6'-en-1'-yl)-cyclohexanol are added dropwise, at 80° C, to 50 ml of 50% strength H$_2$SO$_4$ and the reaction mixture is stirred for 5 minutes at 80° C and is then worked up by the method described in Example 4. 5 g (corresponding to 45% of theory) of a mixture of 2,3,6-trimethyl-1-(3',6'-dimethyl-oct-1'-yn-3',6'-dien-1'-yl)-cyclohex-1(6)-ene and 2,3,6-trimethyl-1-(6'-methyl-3'-methylene-oct-1'-yn-6'-en-1'-yl)-cyclohex-1(6)-ene of boiling point 105°–108° C/0.2 mm Hg are obtained.

EXAMPLE 19

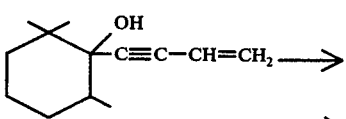

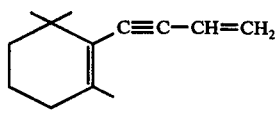

20 g of 2,2,6-trimethyl-1-(but-1'-yn-3'-en-1'-yl)-cyclohexanol are added dropwise, at 80° C, to 100 ml of 50% strength sulfuric acid. The reaction mixture is then stirred for 5 minutes and is worked up by the method described in Example 4. Fractional distillation gives 11.5 g (corresponding to 64% of theory) of 2,6,6-trimethyl-1-(but-1'-yn-3'-en-1'-yl)-cyclohex-1-ene of boiling point 48° C/0.2 mm Hg and refractive index $n_D^{25} = 1.5213$. The IR-spectroscopic data and NMR-spectroscopic data and the elementary analysis confirm the structure. The gas chromatogram shows only one peak. Fragrance note: herbaceous, fruity, somewhat sour, coniferous.

A small amount (<5% of theory) of $\beta$-damascone is formed as a by-product.

EXAMPLE 20

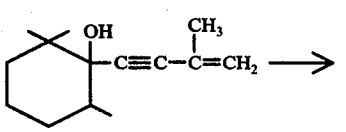

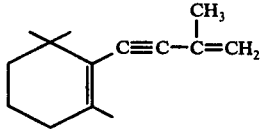

77 g of 2,2,6-trimethyl-1-(3'-methyl-but-1'-yn-3'-en-1'-yl)-cyclohexanol are added dropwise, at 80° C, to 200 ml of 50% strength sulfuric acid. The reaction mixture is then stirred for 30 minutes at 80° C and is worked up by the method described in Example 4. Subsequent fractional distillation gives 47.5 g (corresponding to 68% of theory) of 2,6,6-trimethyl-1-(3'-methyl-but-1'-yn-3'-en-1'-yl)-cyclohex-1-ene of boiling point 57°–59° C/0.15 mm Hg and refractive index $n_D^{25} = 1.5172$. Fragrance note: woody, coniferous, resinous.

If the dehydration of the said cyclohexanol is carried out with 18% strength aqueous HCl by the method of Example 1, with p-toluenesulfonic acid in chloroform by the method of Example 2, or with 60% strength formic acid by the method of Example 3, virtually the same results are acheived.

EXAMPLE 21

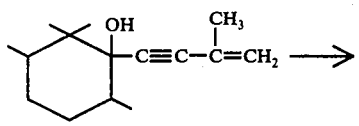

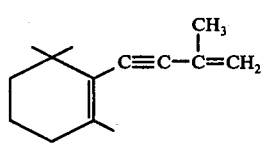

25 g of 2,2,6-trimethyl-1-(3'-methyl-but-1'-yn-3'-en-1'-yl)-cyclohexanol in 100 ml of CHCl$_3$ are boiled with 2 g of anhydrous ZnCl$_2$ under a water separator, 2 ml of water are eliminated in the course of 2 hours. The reaction mixture is washed with water, dried and concentrated. Subsequent fractional distillation gives 12.5 g (corresponding to 55% of theory) of 2,6,6-trimethyl-1-(3'-methyl-but-1'-yn-3'-en-1'-yl)-cyclohex-1-ene.

EXAMPLE 22

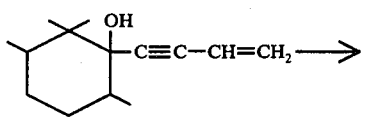

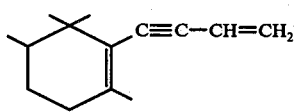

21 g of 2,2,3,6-tetramethyl-1-(but-1'-yn-3'-en-1'-yl)-cyclohexanol are added dropwise, at 80° C, to 80 ml of 50% strength H$_2$SO$_4$ and the reaction mixture is stirred for 5 minutes. It is then extracted with petroleum ether and the petroleum ether extract is washed neutral with NaHCO$_3$ solution, dried and concentrated. Fractional distillation gives 12.5 g (corresponding to 65% of theory) of 2,2,3,6-tetramethyl-1-(but-1'-yn-3'-en-1'-yl)-cyclohex-5-ene of boiling point 55°–57° C/0.2 mm Hg and refractive index $n_D^{25} = 1.5250$. Fragrance note: green, leathery.

EXAMPLE 23

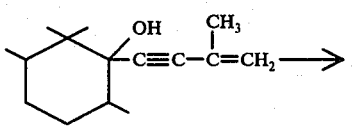

22 g of 2,2,3,6-tetramethyl-1-(3'-methyl-but-1'-yn-3'-en-1'-yl)-cyclohexanol and 5 g of strongly acid ion exchanger (Merck Lewatit S 1080) in 100 ml of 50% strength aqueous acetic acid are boiled under reflux for 2 hours. The ion exchange resin is then filtered off, the solution is extracted with petroleum ether and the petroleum ether extract is neutralized with NaHCO$_3$ solution, dried and concentrated.

Subsequent fractional distillation gives 15.3 g (corresponding to 76% of theory) of 2,2,3,6-tetramethyl-1-(3'-methyl-but-1'-yn-3'-en-1'-yl)-cyclohex-5-ene of boiling point 70°–72° C/0.25 mm Hg. Fragrance note: spicy, woody, tart, herbaceous, faintly leathery.

The IR-spectroscopic data and NMR- spectroscopic data and the elementary analysis confirm the structure; the gas chromatogram shows only 1 peak.

EXAMPLE 24

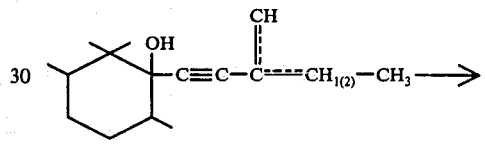

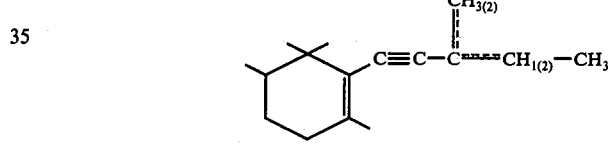

30 g of a mixture of 2,2,3,6-tetramethyl-1-(3'-methyl-pent-1'-yn-3'-en-1'-yl)-cyclohexanol and 2,2,3,6-tetramethyl-1-(3'-methylene-pent-1'-yn-1'-yl)-cyclohexanol in 100 ml of toluene are heated to the boil, with 2 g of anhydrous CuSO$_4$, under a water separator, until no further water separates (3 hours). The mixture is then filtered, concentrated and subject to fractional distillation. 22 g (corresponding to 79% of theory) of a mixture of 2,2,3,6-tetramethyl-1-(3'-methyl-pent-1'-yn-3'-en-1'-yl)-cyclohex-5-ene and 2,2,3,6-tetramethyl-1-(3'-methylene-pent-1'-yn-1'-yl)-cyclohex-5-ene, of boiling 76°–77° C/0.2 mm Hg and refractive index $n_D^{25} = 1.5210$, are obtained. The gas chromatogram shows three isomers. Fragrance note: balsamic, woody.

EXAMPLE 25

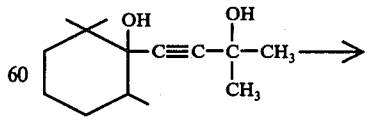

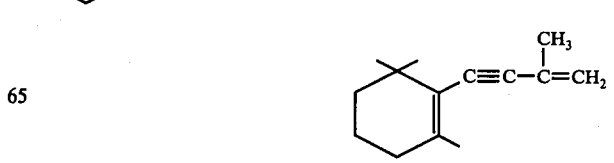

13.5 g of 2,2,6-trimethyl-1-(3'-methyl-3'-hydroxy-but-1'-yn-3'-en-1'-yl)-cyclohexanol are added dropwise, at 80° C, to 50 ml of 50% strength H₂SO₄ and the reaction mixture is stirred for a further 15 minutes at 80° C. It is then extracted with petroleum ether and the petroleum ether extract is washed neutral, dried and concentrated. Fractional distillation gives 6 g (corresponding to 71% of theory) of 2,2,6-trimethyl-1-(3'-methyl-but-1'-yn-3'-en-1'-yl)-cyclohex-5-ene.

EXAMPLE 26

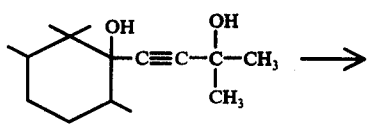

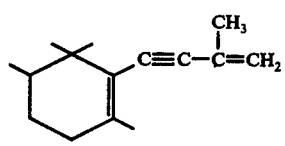

7 g of 2,2,3,6-tetramethyl-1-(3'-methyl-3'-hydroxy-but-1'-yn-1'-yl)-cyclohexanol are reacted with 50 ml of 50% strength H₂SO₄ by the method of Example 12. 3.7 g (corresponding to 61% of theory) of 2,2,3,6-tetramethyl-1-(3'-methyl-but-1'-yn-3'-en -1'-yl)-cyclohex-5-ene and 1.5 g (corresponding to 21% of theory) of the corresponding β-damascone are obtained.

EXAMPLE 27

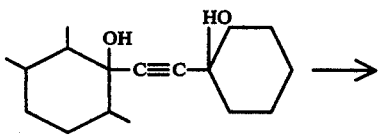

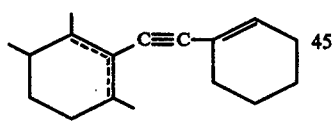

42 g of 1-(2,3,6-trimethyl-1-hydroxy-cyclohex-1-yl)-2-(1-hydroxy-cyclohex-1-yl)-acetylene are added dropwise, at 80° C, to 200 ml of 50% strength H₂SO₄ and the resulting mixture is stirred for 30 minutes at 80° C. It is then extracted with petroleum ether and the petroleum ether extract is washed neutral, dried and concentrated. Fractional distillation gives 23.1 g (corresponding to 55% of theory) of 1-(2',3',6'-trimethyl-cyclohex-1'(5')-en-1'-yl)-2-cyclohex-1-en-1-en-1-yl)-acetylene.

EXAMPLE 28

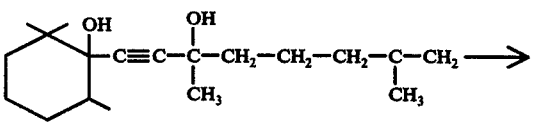

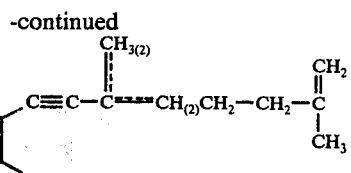

41 g of 1-(2,2,6-trimethyl-1-hydroxy-cyclohex-1-yl)-3,7-dimethyl-3-hydroxy-oct-1-yn-7-ene are added dropwise, at 80° C, to 200 ml of 30% strength H₂SO₄ and the mixture is then stirred for 30 minutes at 80° C. Working up by the method of Example 14 gives 18 g (corresponding to 50% of theory) of a mixture of 2,2,6-trimethyl-1-(3',7'-dimethyl-oct-1'-yn-3',7'-dien-1'-yl)-cyclohex-5-ene and 2,2,6-trimethyl-1-(3'-methylene-4'-methyl-oct-1'-yn-7'-en-1'-yl)-cyclohex-5-ene of boiling point 92°-98° C/0.01 mm Hg, which is contaminated with small amounts of the ketone starting material.

What we claim is:
1. A compound selected from the group consisting of

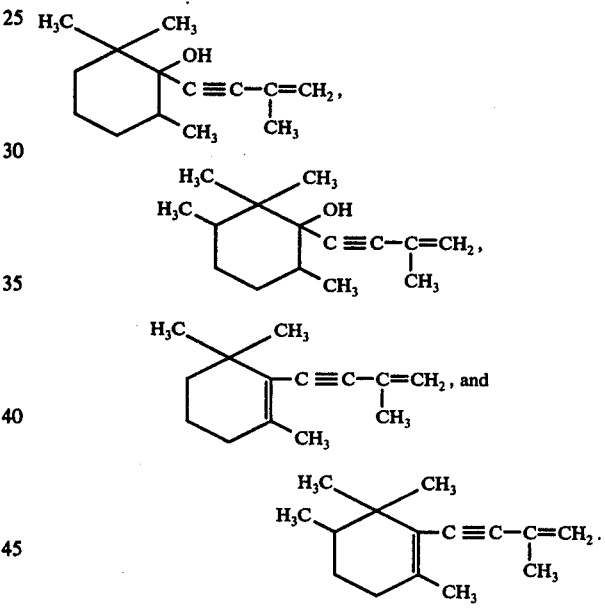

2. A compound as claimed in claim 1 of the formula:

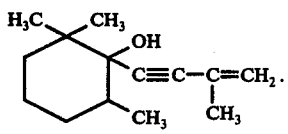

3. A compound as claimed in claim 1 of the formula:

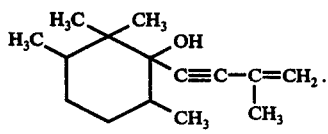

4. A compound as claimed in claim 1 of the formula:

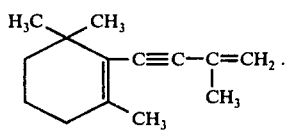
5. A compound as claimed in claim 1 of the formula:
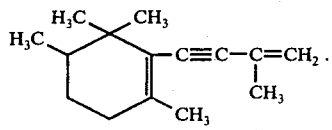
* * * * *